United States Patent [19]

von Sprecher et al.

[11] Patent Number: 5,177,257
[45] Date of Patent: Jan. 5, 1993

[54] BENZOCYCLOALKENECARBOXYLIC ACID AND PROCESS FOR ITS PREPARATION

[75] Inventors: Andreas von Sprecher, Oberwil; Hansjürg Wetter, Therwil, both of Switzerland

[73] Assignee: Ciba-Geigy Corporation, Ardsley, N.Y.

[21] Appl. No.: 776,385
[22] PCT Filed: Mar. 19, 1991
[86] PCT No.: PCT/CH91/00064
    § 371 Date: Nov. 20, 1991
    § 102(e) Date: Nov. 20, 1991
[87] PCT Pub. No.: WO91/14671
    PCT Pub. Date: Oct. 3, 1991

[30] Foreign Application Priority Data

Mar. 27, 1990 [CH] Switzerland ............. 1010/90

[51] Int. Cl.⁵ ............................................. C07C 57/00
[52] U.S. Cl. ................................. 562/401; 562/402
[58] Field of Search ............................. 562/401, 402

[56] References Cited

U.S. PATENT DOCUMENTS

4,523,030  6/1985  Haas ................................. 562/460

FOREIGN PATENT DOCUMENTS

132566  2/1985  European Pat. Off. .

OTHER PUBLICATIONS

Ullmanns Encyklopädie Der Technischen Chemie, 4th Ed., vol. 17, pp. 451–454 (1979).

*Primary Examiner*—Paul J. Killos
*Attorney, Agent, or Firm*—Irving M. Fishman; Karen G. Kaiser

[57] ABSTRACT

The novel (S)-4-(2-bromobenzoyl)-5-hydroxy-benzocyclobutene-1-carboxylic i.e. the compound of the formula

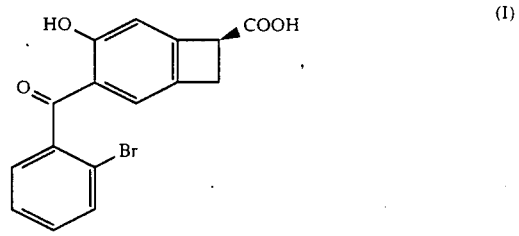

in free form or in salt form, can be used as active ingredient in pharmaceutical preparations and can be prepared by a novel process, which is characterized in that racemic 4-(2-bromobenzoyl)-5-hydroxy-benzocyclobutene-1-carboxylic acid is reacted at elevated temperature with at least the equimolar amount of quinine in an alcoholic solvent for from approximately 6 to approximately 48 hours, the quinine salt of the (S)-4-(2-bromobenzoyl)-5-hydroxy-benzocyclobutene-1-carboxylic acid, precipitated in crystalline form as the direct reaction product, is separated from the reaction mixture, and the (S)-4-(2-bromobenzoyl)-5-hydroxy-benzocyclobutene-1-carboxylic acid is set free from this salt by acid treatment in a customary manner, and, if desired, this free acid is converted into a salt.

11 Claims, No Drawings

BENZOCYCLOALKENECARBOXYLIC ACID AND PROCESS FOR ITS PREPARATION

The invention relates to the novel (S)-4-(2-bromobenzoyl)-5-hydroxy-benzocyclobutene-1-carboxylic acid, i.e. the compound of the formula

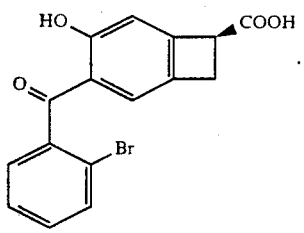

in free form or in salt form, to the use of this compound, to a process for the preparation of this compound and to pharmaceutical preparations containing the compound I in free form or in the form of a pharmaceutically acceptable salt.

The compound I can be in the form of a salt, in particular a pharmaceutically acceptable salt. Corresponding salts are salts with bases. Suitable salts with bases are, for example, metal salts, such as alkali metal salts, for example sodium or potassium salts, or such as alkaline earth metal salts, for example calcium or magnesium salts, or salts with ammonia, with an organic amine, such as morpholine, thiomorpholine, piperidine, pyrrolidine or an aliphatic amine which, if desired, is C-hydroxylated, for example a mono-, di- or tri-lower alkylamine, such as methyl-, ethyl- or diethylamine, a mono-, di- or tri-hydroxy-lower alkylamine, such as ethanol-, diethanol- or triethanolamine, tris(hydroxymethyl)methylamine or 2-hydroxy-tert-butylamine, an N-(hydroxy-lower alkyl)-N,N-di-lower alkylamine, such as 2-(dimethylamino)ethanol, or an N-(polyhydroxy-lower alkyl)-N-lower alkylamine, such as D-glucamine, or with a quaternary ammonium base, such as a quaternary aliphatic ammonium hydroxide, for example tetrabutylammonium hydroxide. Salts which are not suitable for pharmaceutical uses and which are employed, for example, for the isolation or purification, respectively, of the compound I, in free form or in the form of a pharmaceutically acceptable salt, are also included.

The racemic 4-(2-bromobenzoyl)-5-hydroxy-benzocyclobutene-1-carboxylic acid, i.e. the 1:1 enantiomer mixture of (R)- and (S)-4-(2-bromobenzoyl)-5-hydroxy-benzocyclobutene-1-carboxylic acid is known and is proposed, for example in the European Patent Application No. 0 132 566, as an antinociceptive and antiinflammatory pharmaceutical active ingredient having prostaglandin synthesis-inhibiting properties. The novel (S)-4-(2-bromobenzoyl)-5-hydroxy-benzocyclobutene-1-carboxylic acid, in free form or in the form of a pharmaceutically acceptable salt, also has valuable pharmacological properties, for example antinociceptive, antiinflammatory and prostaglandin synthesis-inhibiting activities, to an extent which is comparable to the extent of the activities of the known racemate. Thus, for example, (S)-4-(2-bromobenzoyl)-5-hydroxy-benzocyclobutene-1-carboxylic acid has corresponding desired effects in the writhing test model (induction by phenyl-p-benzoquinone) on the mouse [in accordance with J. Pharmacol. exp. Therap. 125, 237 (1959)], where the $ED_{50}$ is 5 mg/kg p.o., and also in the adjuvant arthritis test on the rat, in which an $ED_{40}$ of 0.5 mg/kg p.o. is found. Additionally, compared with the known racemate, the (S)-enantiomer provided according to the invention has, however, surprising therapeutic advantages. In particular, the (S)-enantiomer is accumulated in the fatty tissue to a smaller extent. Thus, comparison experiments with $^{14}C$-labelled (S)-4-(2-bromobenzoyl)-5-hydroxy-benzocyclobutene-1-carboxylic acid and $^{14}C$-labelled racemic 4-(2-bromobenzoyl)-5-hydroxy-benzocyclobutene-1-carboxylic acid on the rat show that on daily administration of in each case 5 mg/kg p.o. over a period of 10 days, radioactive material is incorporated into the fatty tissue on administration of the (S)-enantiomer in a lower concentration than on administration of the racemate. In particular with respect to a chronic administration of the active ingredient, this is to be valued as a considerable therapeutic advantage of the (S)-enantiomer over the racemate.

The compound I, in free form or in the form of a pharmaceutically acceptable salt, can accordingly be used, for example, as active ingredient in antinociceptive, antiinflammatory and prostaglandin synthesis-inhibiting pharmaceutical compositions, which are used, for example, for the treatment of inflammations, such as inflammatory diseases of the rheumatic type, for example chronic arthritis. The invention thus relates to the use of the compound I, in free form or in the form of a pharmaceutically acceptable salt, for the preparation of corresponding medicaments and for the therapeutic treatment of inflammations, such as inflammatory diseases of the rheumatic type, for example chronic arthritis. The preparation of the medicaments also includes the commercial preparation of the active substances.

In the European Patent Application No. 0 132 566, it is stated that the racemic 4-(2-bromobenzoyl)-5-hydroxy-benzocyclobutene-1-carboxylic acid can be separated into the enantiomers by known methods, for example by reaction "with an optically active base that forms salts with the racemic acid and separation of the salts obtained in this manner, for example on the basis of their differing solubilities, into the diastereomers, from which the antipodes" can "be set free by the action of suitable agents". However, more detailed information about the nature of the optically active base to be used is lacking in the European Patent Application No. 0 132 566. If, for example, quinine is used as the optically active base and customary methods of fractional crystallisation are carried out, only moderate yields of (S)-4-(2-bromobenzoyl)-5-hydroxy-benzocyclobutene-1-carboxylic acid are obtained (see Comparison Example 1). The yield of the desired (S)-enantiomer cannot be improved even by increasing the number of crystallisation steps (see Comparison Example 2).

It has now surprisingly been found that (S)-4-(2-bromobenzoyl)-5-hydroxy-benzocyclobutene-1-carboxylic acid of high to complete, for example at least 85%, i.e. 85% to 100%, such as approximately 90% to approximately 99%, for example at least 92%, optical purity is obtained in yields of over 90% of theory if racemic 4-(2-bromobenzoyl)-5-hydroxy-benzocyclobutene-1-carboxylic acid is reacted at elevated temperature with at least the equimolar amount of quinine in an alcoholic solvent for from approximately 6 to approximately 48 hours, the quinine salt of the (S)-4-(2-bromobenzoyl)-5-hydroxy-benzocyclobutene-1-carboxylic acid, precipitated in crystalline form as the direct reaction product, is separated from the reaction mixture, and the (S)-4-(2-bromobenzoyl)-5-hydroxy-benzocyclobutene-1-carboxylic acid is set free from this salt by acid treatment in a customary manner.

The invention therefore furthermore relates to a novel process for the preparation of the compound I, in free form or in salt form, characterised in that racemic 4-(2-bromobenzoyl)-5-hydroxy-benzocyclobutene-1-carboxylic acid is reacted at elevated temperature with at least the equimolar amount of quinine in an alcoholic solvent for from approximately 6 to approximately 48 hours, the quinine salt of the (S)-4-(2-bromobenzoyl)-5-hydroxy-benzocyclobutene-1-carboxylic acid, precipitated in crystalline form as the direct reaction product, is separated from the reaction mixture, and the (5)-4-(2-bromobenzoyl)-5-hydroxy-benzocyclobutene-1-carboxylic acid is set free from this salt by acid treatment in a customary manner, and, if desired, this free acid is converted into a salt.

Suitable alcoholic solvents are in particular lower alkanols, i.e. $C_1-C_7$alkanols, such as $C_1-C_4$alkanols, for example methanol, ethanol, propanol, isopropanol or butanol, in particular ethanol. The amount of the alcoholic solvent is not critical; however, at least the amount of alcohol necessary for complete dissolution of the components is required. For example, approximately 8 to approximately 50 ml, preferably approximately 20 to approximately 30 ml, of the alcoholic solvent are estimated per g of racemic 4-(2-bromobenzoyl)-5-hydroxy-benzocyclobutene-1-carboxylic acid.

The reaction time amounts to from approximately 6 to approximately 48 hours, in most cases advantageously from approximately 12 to approximately 24 hours.

The reaction temperature is not critical, provided that it is significantly elevated compared with the room temperature. The reaction is advantageously carried out, for example, in a temperature range of from approximately 50° to approximately 120° C., in particular between approximately 60° and approximately 90° C., preferably at the boiling temperature of the alcoholic solvent used.

The amount of quinine is not critical, provided that at least the equimolar amount of quinine is employed. For example, 1.0 time to approximately 1.5 times, preferably approximately 1.05 times to approximately 1.3 times, in particular approximately 1.15 times to approximately 1.25 times, the molar amount of quinine proves favourable.

The separation of the quinine salt of (S)-4-(2-bromobenzoyl)-5-hydroxy-benzocyclobutene-1-carboxylic acid, precipitated according to the process in crystalline form as the direct reaction product, from the reaction mixture is carried out in a customary manner, for example by filtration, suction filtration or centrifugation.

The liberation of the (S)-4-(2-bromobenzoyl)-5-hydroxy-benzocyclobutene-1-carboxylic acid, by acid treatment of its quinine salt obtained according to the process, is carried out in a customary manner, for example by treatment with a mineral acid, such as a hydrohalic acid, for example hydrochloric acid. In this process, at least the equimolar amount, i.e. at least once, for example approximately twice to approximately 10 times, in particular approximately twice to approximately 5 times, the molar amount of acid is used and the reaction is advantageously carried out in a two-phase system, formed from water and a water-immiscible or only partially water-miscible organic solvent, such as an aliphatic alcohol, such as a $C_4-C_7$alkanol, for example butanol, isobutanol, sec-butanol, tert-butanol or a pentanol, hexanol or heptanol, a lower fatty acid ester, such as a $C_2-C_7$alkanoic acid-$C_1-C_4$alkyl ester, for example ethyl acetate, an aromatic or araliphatic hydrocarbon, for example benzene or an alkyl derivative thereof, such as toluene or xylene, a halogenated aliphatic hydrocarbon, such as a halo-$C_1-C_4$alkane, for example di- or trichloromethane, or an aliphatic ether, such as a di-$C_1-C_4$alkyl ether, for example tert-butyl methyl ether.

In a preferred embodiment of the process according to the invention, a solution of racemic 4-(2-bromobenzoyl)-5-hydroxy-benzocyclobutene-1-carboxylic acid and 1.0 time to approximately 1.5 times the molar amount, i.e. 0.94 to approximately 1.41 kg per kg of acid, of quinine in approximately 8 times to approximately 50 times the amount by volume, i.e. approximately 8 to approximately 50 l per kg of acid, of a $C_1-C_4$alkanol is heated to from approximately 60° to approximately 90° C. for from approximately 6 to approximately 48 hours, the quinine salt of (S)-4-(2-bromobenzoyl)-5-hydroxy-benzocyclobutene-1-carboxylic acid, precipitated in crystalline form as the direct reaction product, is separated from the reaction mixture in a customary manner, and the (s)-4-(2-bromobenzoyl)-5-hydroxy-benzocyclobutene-1-carboxylic acid is set free by acid treatment in a customary manner of its quinine salt obtained according to the process.

In a particularly preferred embodiment of the process according to the invention, a solution of racemic 4-(2-bromobenzoyl)-5-hydroxy-benzocyclobutene-1-carboxylic acid and approximately 1.05 times to approximately 1.3 times the molar amount, i.e. approximately 0.99 to approximately 1.22 kg per kg of acid, of quinine in approximately 20 times to approximately 30 times the amount by volume, i.e. approximately 20 to approximately 30 l per kg of acid, of ethanol is heated to the boiling temperature of the ethanol for from approximately 12 to approximately 24 hours, the quinine salt of (S)-4-(2-bromobenzoyl)-5-hydroxy-benzocyclobutene-1-carboxylic acid, precipitated in crystalline form as the direction reaction product, is separated from the reaction mixture in a customary manner, and the (S)-4-(2-bromobenzoyl)-5-hydroxy-benzocyclobutene-1-carboxylic acid is set free by treatment of its quinine salt obtained according to the process with approximately twice to approximately 5 times the molar amount of hydrochloric acid in a two-phase system formed from water and tert-butyl methyl ether.

The free (S)-4-(2-bromobenzoyl)-5-hydroxy-benzocyclobutene-1-carboxylic acid obtainable according to the process can be converted into one of its salts in a manner known per se, for example by reaction of a solution of the free acid in a suitable solvent or solvent mixture with a base, such as an alkali metal hydroxide, a metal carbonate or hydrogencarbonate, ammonia or another of the salt-forming bases mentioned hereinbefore, or with a suitable ion exchange reagent.

The compound I can be obtained in free form or in salt form, depending on the procedure and the reaction conditions. As a result of the close relationship between the compound I in the free from and in the form of its salts, the free compound I or its salts above and below is also to be understood as meaning accordingly and appropriately, where relevant, the corresponding salts or the free compound I.

The compound I, including its salts, can also be obtained in the form of hydrates and/or can include other solvents, for example those used for crystallisation.

The invention also relates to those embodiments of the process in which a compound obtainable as an intermediate at any stage of the process is used as the starting substance and the missing steps are carried out.

The invention likewise relates to novel intermediates for the preparation of the compound I, to their use and to a process for their preparation.

The compound I and its pharmaceutically acceptable salts can be used, preferably in the form of pharmaceutically acceptable formulations, in a method for the prophylactic and/or therapeutic treatment of the animal or human body, in particular as antinociceptive, antiinflammatory and prostaglandin synthesis-inhibiting pharmaceutical compositions.

The invention thus likewise relates to pharmaceutical preparations containing the compound I as the active ingredient in the free form or in the form of a pharmaceutically acceptable salt, and to a process for their preparation. These pharmaceutical preparations are those for enteral, such as oral and furthermore rectal, or parenteral administration to warm-blooded animals, the preparation containing the pharmacological active ingredient by itself or together with customary pharmaceutical auxiliaries. The pharmaceutical preparations contain, for example, from about 0.1% to 100%, preferably from about 1% to about 50%, of the active ingredient. Pharmaceutical preparations for enteral or parenteral administration are, for example, those in unit dose forms, such as sugar-coated tablets, tablets, capsules or suppositories, and furthermore ampoules. These are prepared in a manner which is known per se, for example by means of conventional mixing, granulating, sugar-coating, dissolving or lyophilising processes. Pharmaceutical preparations which are suitable for oral administration can thus be obtained by combining the active ingredient with solid carriers, if appropriate granulating the resulting mixture, and processing the mixture or granules, if desired or necessary after addition of suitable excipients, to give tablets or sugar-coated tablet cores.

Suitable carriers are in particular fillers, such as sugars, for example lactose, sucrose, mannitol or sorbitol, cellulose preparations and/or calcium phosphates, for example tricalcium phosphate or calcium hydrogen phosphate, and also binders, such as starch pastes, using, for example, maize starch, wheat starch, rice starch or potato starch, gelatin, tragacanth, methylcellulose and/or polyvinylpyrrolidone, and, if desired, disintegrators, such as the abovementioned starches, and also carboxymethyl starch, crosslinked polyvinylpyrrolidone, agar or alginic acid or a salt thereof, such as socium alginate. Excipients are chiefly glidants and lubricants, for example silicic acid, talc, stearic acid or salts thereof, such as magnesium stearate or calcium stearate, and/or polyethylene glycol. Sugar-coated tablet cores are provided with suitable coatings which can be resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or sugar coatings, for example to identify or indicate different doses of active ingredient.

Further pharmaceutical preparations capable of oral administration are dry-filled capsules of gelatin and also soft, sealed capsules made from gelatin and a plasticiser, such as glycerol or sorbitol. The dry-filled capsules can contain the active ingredient in the form of granules, for example in admixture with fillers, such as lactose, binders, such as starches, and/or lubricants, such as talc or magnesium stearate, and if appropriate stabilisers. In soft capsules, the active ingredient is preferably dissolved or suspended in suitable liquids, such as fatty oils, paraffin oil or liquid polyethylene glycols, to which stabilisers can also be added.

Suitable pharmaceutical preparations for rectal administration are, for example, suppositories, which consist of a combination of the active ingredient with a suppository base. Examples of suitable suppository bases are natural or synthetic triglycerides, paraffin hydrocarbons, polyethylene glycols and higher alkanols. Gelatin rectal capsules, which contain a combination of the active ingredient with a base material, can furthermore also be used. Suitable base materials are, for example, liquid triglycerides, polyethylene glycols and paraffin hydrocarbons.

Suitable forms for parenteral administration are, in particular, aqueous solutions of an active ingredient in water-soluble form, for example a water-soluble salt, and furthermore suspensions of the active ingredient, such as corresponding oily injection suspensions, in which case suitable lipophilic solvents or vehicles, such as fatty oils, for example sesame oil, or synthetic fatty acid esters, for example ethyl oleate or triglycerides, are used, or aqueous injection suspensions which contain viscosity-increasing substances, for example sodium carboxymethylcellulose, sorbitol and/or dextran, and if appropriate also stabilisers.

The dosage of the active ingredient can depend on various factors, such as the mode of administration, the warm-blooded species, the age and/or condition of the individual. In the normal case, an approximate daily dose of about 10 mg to about 250 mg is to be estimated for oral administration to a patient weighing about 75 kg.

The following examples illustrate the invention described above; however, they are not intended to limit this in its scope in any way. Temperatures are stated in degrees Celsius.

EXEMPLARY EMBODIMENT a) 3.47 g (10 mmol) of racemic 4-(2-bromobenzoyl)-5-hydroxybenzocyclobutene-1-carboxylic acid are dissolved in 40 ml of absolute ethanol. The mixture is heated to 70° and a solution of 3.89 g (12 mmol) of quinine in 40 ml of absolute ethanol is added. The temperature of the mixture decreases to 58°. The reaction mixture is heated to reflux with stirring (internal temperature: 77°). After about 30 minutes, the deposition of crystals begins on the vessel wall. The mixture is heated at reflux with stirring for a further 20.5 hours, allowed to cool to room temperature, and filtered with suction, and the filtration residue is washed twice with 5 ml of absolute ethanol each time and dried to constant weight. 6.31 g of the quinine salt of (S)-4-(2-bromobenzoyl)-5-hydroxy-benzocyclobutene-1-carboxylic acid are thus obtained [yield: 94.1% of theory; (S):(R) ratio according to HPLC analysis: $\geq 96:4$].

b) A suspension of 61.5 g (91.7 mmol) of the quinine salt of (S)-4-(2-bromobenzoyl)-5-hydroxy-benzocyclobutene-1-carboxylic acid obtained according to step a) in 200 ml of tert-butyl methyl ether is treated at 0° with 100 ml of 2N hydrochloric acid while stirring. The organic phase is separated off and the aqueous phase is extracted by shaking with 20 ml of tert-butyl methyl ether. The organic phases are combined, washed with water until neutral, dried over sodium sulfate and evaporated to dryness under reduced pressure. The residue consists of 35.2 g of a highly viscous yellowish oil, which still contains some solvent and is crystallised from hexane. 31.4 g of (S)-4-(2-bromobenzoyl)-5-hydroxy-benzocyclobutene-1-carboxylic acid are thus obtained [m.p.: 104° to 105°; $[\alpha]_{20}^D$: $-24.8°$ (1% in $CHCl_3$); (S):(R) ratio according to HPLC analysis: $\geq 96.4$]. The total yield over both steps is 93.1% of theory.

COMPARISON EXAMPLE 1

17.35 g (50.1 mmol) of racemic 4-(2-bromobenzoyl)-5-hydroxy-benzocyclobutene-1-carboxylic acid are suspended in 250 ml of absolute ethanol. The suspension is warmed to 40°, 8.5 g (26.2 mmol) of quinine are added, and the mixture is heated to reflux. The quinine salt of 4-(2-bromobenzoyl)-5-hydroxy-benzocyclobutene-1-carboxylic acid already begins to precipitate at a temperature of from 60° to 65° C. The reaction mixture is stirred under reflux for 5 minutes and then allowed to cool to room temperature in the course of 1 hour, the white suspension is filtered with suction, and the filter cake is washed twice with 30 ml of absolute ethanol each time and sucked dry. The quinine salt of 4-(2-bromobenzoyl)-5-hydroxy-benzocyclobutene-1-carboxylic acid is thus obtained (crystallisation step 1). This salt is dissolved in 200 ml of ethyl acetate, and the solution is extracted by shaking with 100 ml of 2N hydrochloric acid, washed twice with 50 ml of water each time, dried over magnesium sulfate and evaporated under reduced pressure. The 4-(2-bromobenzoyl)-5-hydroxy-benzocyclo-butene-1-carboxylic acid thus obtained (crystallisation step 1) is dissolved in 100 ml of absolute ethanol, the solution is treated with 8.1 g (25 mmol) of quinine, and the reaction mixture is heated to reflux and stirred under reflux for 5 minutes. The reaction mixture is allowed to cool to room temperature in the course of 1 hour and is filtered with suction, the filter cake is washed twice with 20 ml of absolute ethanol each time and sucked dry. The quinine salt of (S)-4-(2-bromobenzoyl)-5-hydroxy-benzocyclobutene-1-carboxylic acid is thus obtained (crystallisation step 2). This salt is dissolved in 200 ml of ethyl acetate, and the solution is extracted by shaking with 100 ml of 2N hydrochloric acid, washed twice with 50 ml of water each time, dried over magnesium sulfate and evaporated under reduced pressure.

The crude (S)-4-(2-bromobenzoyl)-5-hydroxy-benzocyclo-butene-1-carboxylic acid thus obtained (crystallisation step 2) is dissolved in diethyl ether, and the solution is treated with petroleum ether until the onset of turbidity. The mixture is stirred for some time and filtered with suction, and the filter cake is dried overnight under reduced pressure at 40°. 4.7 g of pure (S)-4-(2-bromobenzoyl)-5-hydroxy-benzocyclobutene-1-carboxylic acid are thus obtained [m.p.: 103° to 104°; $[\alpha]_{20}^D$: $-24.1° \pm 1.1°$; (S):(R) ratio according to HPLC analysis: $\geq 99:1$; total yield: 27.1% of theory].

COMPARISON EXAMPLE 2

34.7 g (100 mmol) of racemic 4-(2-bromobenzoyl)-5-hydroxy-benzocyclobutene-1-carboxylic acid are dissolved in 800 ml of absolute ethanol. The solution is warmed to 40°, 32.4 g (100 mmol) of quinine are added, and the reaction mixture is heated to reflux. The quinine salt of 4-(2-bromobenzoyl)-5-hydroxy-benzocyclobutene-1-carboxylic acid already begins to precipitate at a temperature of 70°. The reaction mixture is stirred under reflux for 5 minutes and then allowed to cool to 35° in the course of 1 hour, the white suspension is filtered with suction, and the filter cake is washed twice with 100 ml of absolute ethanol each time and sucked dry. The quinine salt of 4-(2-bromobenzoyl)-5-hydroxy-benzocyclobutene-1-carboxylic acid is thus obtained (crystallisation step 1). This salt is dissolved in 200 ml of ethyl acetate, and the solution is extracted by shaking with 200 ml of 2N hydrochloric acid, washed twice with 50 ml of water each time, dried over magnesium sulfate and evaporated under reduced pressure. 24 g of 4-(2-bromobenzoyl)-5-hydroxy-benzocyclobutene-1-carboxylic acid are thus obtained (crystallisation step 1). This acid is dissolved in 800 ml of ethanol, the solution is treated with 22.4 g (69 mmol) of quinine, and the reaction mixture is heated to reflux and stirred under reflux for 5 minutes. The reaction mixture is allowed to cool to 35° in the course of 1 hour and is filtered with suction, and the filter cake is washed twice with 60 ml of absolute ethanol each time and sucked dry. The quinine salt of 4-(2-bromobenzoyl)-5-hydroxy-benzocyclobutene-1-carboxylic acid is thus obtained (crystallisation step 2). This salt is dissolved in 200 ml of ethyl acetate, and the solution is extracted by shaking with 135 ml of 2N hydrochloric acid, washed twice with 50 ml of water each time, dried over magnesium sulfate and evaporated under reduced pressure. 17 g of 4-(2-bromobenzoyl)-5-hydroxy-benzocyclobutene-1-carboxylic acid are thus obtained (crystallisation step 2). This acid is dissolved in 800 ml of absolute ethanol, the solution is treated with 15.9 g (49 mmol) of quinine, and the reaction mixture is heated to reflux and stirred under reflux for 5 minutes. The reaction mixture is allowed to cool to 35° in the course of 1 hour and is filtered with suction, and the filter cake is washed twice with 60 ml of absolute ethanol each time and sucked dry. The quinine salt of 4-(2-bromobenzoyl)-5-hydroxy-benzocyclobutene-1-carboxylic acid is thus obtained (crystallisation step 3). This salt is dissolved in 200 ml of ethyl acetate, and the solution is extracted by shaking with 98 ml of 2N hydrochloric acid, washed twice with 40 ml of water each time, dried over magnesium sulfate and evaporated under reduced pressure. 14 g of 4-(2-bromobenzoyl)-5-hydroxy-benzocyclobutene-1-carboxylic acid are thus obtained (crystallisation step 3). This acid is dissolved in 800 ml of absolute ethanol, the solution is treated with 13.1 g (40 mmol) of quinine, and the reaction mixture is heated to reflux and stirred under reflux for 5 minutes. The reaction mixture is allowed to cool to 35° in the course of 1 hour and is filtered with suction, and the filter cake is washed twice with 60 ml of absolute ethanol each time and sucked dry. The quinine salt of (S)-4-(2-bromobenzoyl)-5-hydroxy-benzocyclobutene-1-carboxylic acid is thus obtained (crystallisation step 4). This salt is dissolved in 200 ml of ethyl acetate, and the solution is extracted by shaking with 81 ml of 2N hydrochloric acid, washed twice with 40 ml of water each time, dried over magnesium sulfate and evaporated under reduced pressure. 10.5 g of crude (S)-4-(2-bromobenzoyl)-5-hydroxy-benzocyclobutene-1-carboxylic acid are thus obtained (crystallisation step 4). This acid is dissolved in diethyl ether and the solution is treated with petroleum ether until the onset of turbidity. The mixture is stirred for some time and filtered with suction, and the filter cake is dried overnight under reduced pressure at 40°. 8.8 g of pure (S)-4-(2-bromobenzoyl)-5-hydroxy-benzocyclobutene-1-carboxylic acid are thus obtained [m.p.: 103° to 104°; $[\alpha]_{20}^D$: $-26.1° \pm 1.0°$; (S):(R) ratio according to HPLC analysis: $\geq 99.5:0.5$; total yield: 25.4% of theory].

PREPARATION EXAMPLE 1

Tablets, each containing as active ingredient 50 mg of (S)-4-(2-bromobenzoyl)-5-hydroxy-benzocyclobutene-1-carboxylic acid or a salt thereof, for example the sodium salt, can be prepared as follows:

| Composition (for 10,000 tablets): | |
|---|---|
| Active ingredient | 500.0 g |
| Lactose | 500.0 g |
| Potato starch | 352.0 g |
| Gelatin | 8.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of the potato starch, and the mixture is moistened with an ethanolic solution of the gelatin and granulated through a sieve. After drying, the remainder of the potato starch, the magnesium stearate, the talc and the silica are admixed and the mixture is compressed to give tablets each of weight 145 mg and active ingredient content 50 mg, which, if desired, can be provided with breaking notches for finer adjustment of the dosage.

PREPARATION EXAMPLE 2

Film-coated tablets, each containing as active ingredient 100 mg of (S)-4-(2-bromobenzoyl)-5-hydroxy-benzocyclobutene-1-carboxylic acid or a salt thereof, for example the sodium salt, can be prepared as follows:

| Composition (for 1000 film-coated tablets): | |
|---|---|
| Active ingredient | 100.0 g |
| Lactose | 100.0 g |
| Maize starch | 70.0 g |
| Talc | 8.5 g |
| Calcium stearate | 1.5 g |
| Hydroxypropylmethylcellulose | 2.36 g |
| Shellac | 0.64 g |
| Water | q.s. |
| Dichloromethane | q.s. |

The active ingredient, the lactose and 40 g of the maize starch are mixed. The mixture is moistened with a paste prepared from 15 g of maize starch and water (with warming), and is granulated. The granules are dried, and the remainder of the maize starch, the talc and the calcium stearate are mixed with the granules. The mixture is compressed to give tablets (weight: 280 mg each) and these are coated with a solution of the hydroxypropylmethylcellulose and the shellac in dichloromethane (final weight of the film-coated tablets: 283 mg each).

PREPARATION EXAMPLE 3

Hard gelatin capsules, each containing as active ingredient 100 g of (S)-4-(2-bromobenzoyl)-5-hydroxy-benzocyclobutene-1-carboxylic acid or a salt thereof, for example the sodium salt, can be prepared as follows:

| Composition (for 1000 capsules): | |
|---|---|
| Active ingredient | 100.0 g |
| Lactose | 250.0 g |
| Microcrystalline cellulose | 30.0 g |
| Sodium lauryl sulfate | 2.0 g |
| Magnesium stearate | 8.0 g |

The sodium lauryl sulfate is sieved into the lyophilised active ingredient through a sieve having a mesh width of 0.2 mm. Both components are intimately mixed. The lactose is then first sieved in through a sieve having a mesh width of 0.6 mm and subsequently the microcrystalline cellulose through a sieve having a mesh width of 0.9 mm. All four components are then intimately mixed for 10 minutes. Finally, the magnesium stearate is sieved in through a sieve having a mesh width of 0.8 mm. After further mixing (3 minutes), 390 mg each of the formulation obtained is filled into hard gelatin capsules of size 0.

PREPARATION EXAMPLE 4

An injection or infusion solution, containing as active ingredient (S)-4-(2-bromobenzoyl)-5-hydroxy-benzocyclobutene-1-carboxylic acid or a salt thereof, for example the sodium salt, can be prepared as follows:

| Composition (for 1000 ampoules): | |
|---|---|
| Active ingredient | 5.0 g |
| Sodium chloride | 22.5 g |
| Phosphate buffer solution (pH: 7.4) | 300.0 g |
| Demineralised water to | 2500.0 ml |

The active ingredient and the sodium chloride are dissolved in 1000 ml of demineralised water. The solution is filtered through a microfilter. The filtrate is treated with the phosphate buffer solution, and the mixture is made up to 2500 ml with demineralised water. To prepare unit dose forms, 2.5 ml of the mixture each time are filled into glass ampoules, which then each contain 5 mg of active ingredient.

What is claimed is:

1. A process for the preparation of (S)-4-(2-bromobenzoyl)-5-hydroxy-benzocyclobutene-1-carboxylic acid, i.e. the compound of the formula

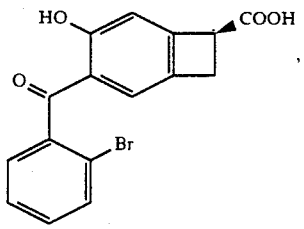

(I)

in free form or in salt form, characterised in that racemic-4-(2-bromobenzoyl)-5-hydroxy-benzocyclobutene-1-carboxylic acid is reacted at elevated temperature with at least the equimolar amount of quinine in an alcoholic solvent for from approximately 6 to approximately 48 hours, the quinine salt of the (S)-4-(2-bromobenzoyl)-5-hydroxy-benzocyclobutene-1-carboxylic acid, precipitated in crystalline form as the direct reaction product, is separated from the reaction mixture, and the (S)-4-(2-bromobenzoyl)-5-hydroxy-benzocyclobutene-1-carboxylic acid is set free from this salt by acid treatment in a customary manner, and, if desired, this free acid is converted into a salt.

2. A process according to claim 1, characterised in that a $C_1$–$C_7$alkanol is used as the alcoholic solvent.

3. A process according to characterised in that approximately 8 to approximately 50 ml of the alcoholic solvent are used per g of racemic 4-(2-bromobenzoyl)-5-hydroxy-benzocyclobutene-1-carboxylic acid.

4. A process according to claim 1 characterised in that the racemic 4-(2-bromobenzoyl)-5-hydroxy-benzocyclobutene-1-carboxylic acid is reacted with quinine in a temperature range of from approximately 50° to approximately 120° C.

5. A process according to claim 1 characterised in that the racemic 4-(2-bromobenzoyl)-5-hydroxy-benzocyclobutene-1-carboxylic acid is reacted with quinine at the boiling temperature of the alcoholic solvent used.

6. A process according to claim 1 characterised in that the racemic 4-(2-bromobenzoyl)-5-hydroxy-benzocyclobutene-1-carboxylic acid is reacted with 1.0 time to approximately 1.5 times the molar amount of quinine.

7. A process according to claim 1 characterised in that the liberation of the (S)-4-(2-bromobenzoyl)-5-hydroxy-benzocyclobutene-1-carboxylic acid from its quinine salt obtained according to the process is carried out by treatment with a mineral acid.

8. A process according to claim 1 characterised in that liberation of the (S)-4-(2-bromobenzoyl)-5-hydroxy-benzocyclobutene-1-carboxylic acid from its quinine salt obtained according to the process the acid employed for the liberation is used at least in the equimolar amount.

9. A process according to claim 1 characterised in that the liberation of the (S)-4-(2-bromobenzoyl)-5-hydroxy-benzocyclobutene-1-carboxylic acid from its quinine salt obtained according to the process is carried out in a two-phase system.

10. A process according to claim 1, characterised in that a solution of racemic 4-(2-bromobenzoyl)-5-hydroxy-benzocyclobutene-1-carboxylic acid and 1.0 time to approximately 1.5 times the molar amount of acid, of quinine in approximately 8 times to approximately 50 times the amount by volume of acid, of a $C_1$–$C_4$alkanol is heated to form approximately 60° to approximately for from approximately 6 to approximately 48 hours, the quinine salt of (S)-4-(2-bromobenzoyl)-5-hydroxylbenzocyclobutene-1-carboxylic acid, precipitated in crystalline form as the direct reaction product, is separated from the reaction mixture in a customary manner, and the (S)-4-(2-bromobenzoyl)-5-hydroxy-benzocyclobutene-1-carboxylic acid is set free by acid treatment in a customary manner of its quinine salt obtained according to the process.

11. A process according to claim 10, characterised in that a solution of racemic 4-(2-bromobenzoyl)-5-hydroxy-benzocyclobutene-1-carboxylic acid and approximately 1.05 times to approximately 1.3 times the molar amount of acid, of quinine in approximately 20 times to approximately 30 times the amount by volume of acid, of ethanol is heated to the boiling temperature of the ethanol for from approximately 12 to approximately 24 hours, the quinine salt of (S)-4-(2-bromobenzoyl)-5-hydroxy-benzocyclobutene-1-carboxylic acid, precipitated in crystalline form as the direct reaction product, is separated from the reaction mixture in a customary manner, and the (S)-4-(2-bromobenzoyl)-5-hydroxy-benzocyclobutene-1-carboxylic acid is set free by treatment of its quinine salt obtained according to the process with approximately twice to the approximately 5 times the molar amount of hydrochloric acid in a two-phase system formed from water and tert-butyl methyl ether.

* * * * *

UNITED STATES PATENT AND TRADEMARK OFFICE
CERTIFICATE OF CORRECTION

PATENT NO. : 5,177,257
DATED : January 5, 1993
INVENTOR(S) : von Sprecher et al

It is certified that error appears in the above-identified patent and that said Letters Patent is hereby corrected as shown below:

Column 10, line 66
In claim 1, line 6, after "racemic" delete "-"
Column 11, lines 13 & 37
In claim 3, line 1, after "a process according to"

insert --claim 1--

In claim 8, line 2, after "in that" insert --in the--
Column 12, lines 13, 14, & 16
In claim 10, line 7, after "heated to" delete "form" and insert --from-- in lieu thereof; in line 8 after "approximately"

insert --90°C--; and in line 10 after "-5-" delete

"hydroxylbenzocyclobutene" and insert -hydroxy-benzocyclobutene-- in lieu thereof.

Signed and Sealed this

Twenty-sixth Day of October, 1993

Attest:

BRUCE LEHMAN

Attesting Officer

Commissioner of Patents and Trademarks